(12) United States Patent
Bousseljot et al.

(10) Patent No.: US 6,491,629 B1
(45) Date of Patent: Dec. 10, 2002

(54) METHOD FOR DETERMINING AT LEAST ONE DIAGNOSTIC PIECE OF INFORMATION FROM SIGNAL PATTERNS OF MEDICAL SENSOR SYSTEMS

(75) Inventors: Ralf Bousseljot, Koenigs Wusterhausen (DE); Dieter Kreiseler, Berlin (DE)

(73) Assignees: Bundesrepublik Deutschland, Vertreten Durch (DE); Den Bundesminister fuer Wirtschaft, Dieser Vertreten Durch (DE); Den Praesidenten der Physiklisch-Technischen Bundesanstalt, Braunschweig (DE)

( * ) Notice: Subject to any disclaimer, the term of this patent is extended or adjusted under 35 U.S.C. 154(b) by 0 days.

(21) Appl. No.: 09/554,100

(22) PCT Filed: Nov. 21, 1998

(86) PCT No.: PCT/DE98/03443
§ 371 (c)(1),
(2), (4) Date: May 25, 2000

(87) PCT Pub. No.: WO99/27463
PCT Pub. Date: Jun. 3, 1999

(30) Foreign Application Priority Data

Nov. 25, 1997 (DE) ......................................... 197 52 094

(51) Int. Cl.⁷ ............................................... A61B 5/00
(52) U.S. Cl. ..................................................... 600/300
(58) Field of Search .................. 600/508–528, 600/300, 547; 128/897–925

(56) References Cited

U.S. PATENT DOCUMENTS

| 4,930,075 A | 5/1990 | Kortas |
| 5,003,983 A | 4/1991 | Dingwall et al. |
| 5,020,540 A | 6/1991 | Chamoun |
| 5,022,404 A | 6/1991 | Hafner |
| 5,025,794 A | 6/1991 | Albert et al. |
| 5,029,082 A | 7/1991 | Shen et al. |
| 5,159,932 A | 11/1992 | Zanetti et al. |
| 5,240,009 A | 8/1993 | Williams |
| 5,259,387 A | 11/1993 | dePinto |

(List continued on next page.)

FOREIGN PATENT DOCUMENTS

| DE | 32 09 850 | 3/1985 |
| DE | 39 27 709 | 3/1990 |
| DE | 41 06 856 | 9/1992 |
| DE | 43 04 269 | 8/1993 |
| DE | 43 10 412 | 7/1994 |
| DE | 196 38 738 | 3/1998 |
| EP | 0 642 760 | 3/1995 |
| WO | WO 97/08989 | 3/1997 |

Primary Examiner—Kevin Shaver
Assistant Examiner—David McCrosky
(74) Attorney, Agent, or Firm—Foley & Lardner

(57) ABSTRACT

A method for evaluating measured periodic or quasiperiodic signals of medical sensor systems. The method comprises digitizing the measured signals with a specific first sampling frequency, normalizing the periods of the measured signals to a predetermined period length, using a database in which previously measured signals are stored after digitization with specific second sampling frequencies and in which medical findings are assigned to the stored signals. If the first and second sampling frequencies are not identical, converting the measured signal of the signals stored in the database so as to have the same sampling frequencies. Also, comparing at least a section of the digitized measured signal with a corresponding section of the signals stored in the database, determining an accumulation of correspondences between stored signals and the measured signals and determining a correspondence accumulation of medical findings assigned to the stores signals and deriving a probability of the presence of a specific medical finding with reference to the measured signal from the degree of accumulation.

12 Claims, 3 Drawing Sheets

U.S. PATENT DOCUMENTS

Figure 1:
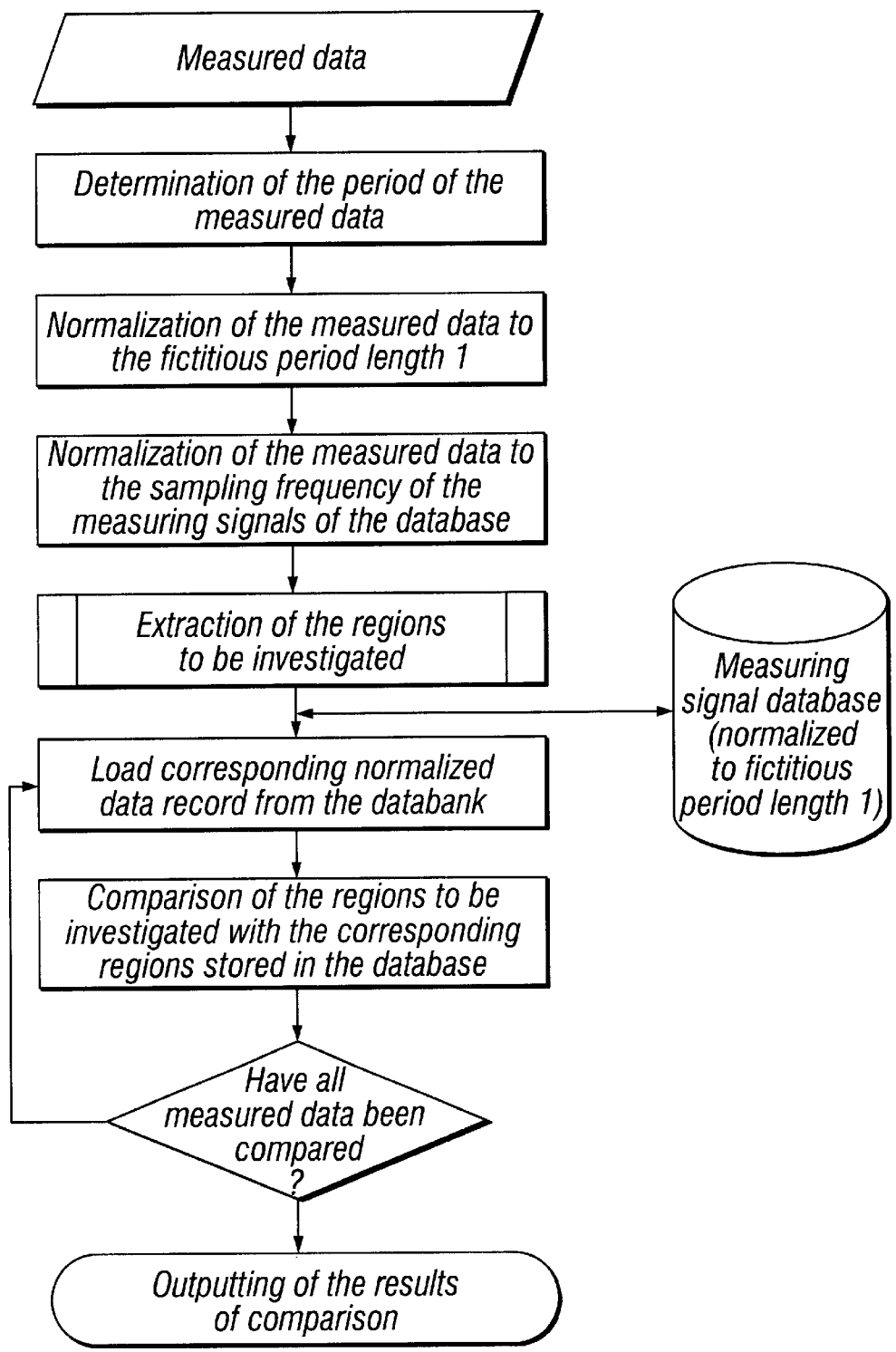

| | | |
|---|---|---|
| 5,277,189 A | 1/1994 | Jacobs |
| 5,280,792 A * | 1/1994 | Leong et al. ............... 128/925 |
| 5,341,811 A | 8/1994 | Cano |
| 5,355,891 A | 10/1994 | Wateridge et al. |
| 5,355,892 A | 10/1994 | Saltzstein et al. |
| 5,357,969 A | 10/1994 | Herleikson |
| 5,419,337 A | 5/1995 | Dempsey et al. |
| 5,437,278 A | 8/1995 | Wilk |
| 5,443,073 A * | 8/1995 | Wang et al. ................ 600/526 |
| 5,469,856 A | 11/1995 | Lundstrom et al. |
| 5,497,780 A | 3/1996 | Zehender |
| 5,680,867 A | 10/1997 | Shimazu et al. |
| 5,749,367 A | 5/1998 | Gamlyn |
| 5,810,014 A * | 9/1998 | Davis et al. ................ 600/508 |
| 5,810,722 A * | 9/1998 | Heikkila .................... 600/300 |
| 5,878,071 A | 3/1999 | Delavaux |
| 5,961,467 A | 10/1999 | Shimazu et al. |
| 6,308,280 B1 | 5/2001 | Clube |
| 6,226,110 B1 | 10/2001 | Joseph et al. |

\* cited by examiner

METHOD FOR DETERMINING AT LEAST ONE DIAGNOSTIC PIECE OF INFORMATION FROM SIGNAL PATTERNS OF MEDICAL SENSOR SYSTEMS

The invention relates to a method for evaluating measured periodic or quasiperiodic signals of medical sensor systems by digitizing the signals and comparing signal sections of the measured signals with stored comparable signal sections.

Characteristics of known technical solutions:

The methods described in the accessible literature for the purpose of establishing the signal pattern similarity of periodic signals of medical sensor systems are generally limited to the signals of the same patient.

It is known in this case to carry out a correlation of ECG signals, measured under normal conditions and filtered, with current ECG signals, which may be defective and/or pathological, of the same [lacuna]. A further example is U.S. Pat. No. 5,240,009. Here, the detection of arrhythmias by comparing averaged and stored waveform complexes with the currently measured ones of the same patient is described. Arrhythmias are also classified in DE 32 09 850. This is performed by comparing the complete profile of the ECG with ECG profiles, previously recorded in a learning phase or calculated, of the patient examined, and the complete storage of an example of the ECG profile for each class of arrhythmias of the patient examined. It is a common feature of all the solutions presented that they permit only the comparison of ECG, or of portions of the ECG, on the same patient.

ECG evaluation systems, for example according to U.S. Pat. No. 5,022,404, detect one or more electrode potentials of electrodes fastened on the patient, and filter and digitize them. Subsequently, these signals are fed via a multiplexer to a microcomputer, present in the ECG evaluation system, with a CPU, main memory etc. Said microcomputer conditions the measured signals, for example by removing the baseline drift in accordance with DE 4,106,856, U.S. Pat. No. 5,357,969, or the removal of muscle artefacts from the ECG in accordance with U.S. Pat. No. 5,259,387. It also calculates the Wilson, Goldberger, Einthoven medical recordings which are required for the medical assessment of an ECG, and/or the Frank orthogonal recordings. In the simplest case, these medical recordings are displayed either on paper strips and/or electronic displays, for example on LCD displays in U.S. Pat. No. 5,022,404, and assessed by the evaluating doctor. Apart from for signal conditioning and display, more intelligent, so-called evaluating electrocardiographs use the microcomputer present in the equipment for the purpose of signal evaluation, signal measurement and, if appropriate, for the purpose of outputting diagnostic information as, for example, in U.S. Pat. No. 5,029,082.

The signal measurement and evaluation is generally performed, as is further described in the patent specifications explained in more detail below, such that the calculated medical recordings are used to determine a number of individual signal parameters, which are important for the cardiological assessment of the ECG, with reference to time duration and amplitude and/or criteria derived therefrom. Problems arise in the case of this determination of individual signal characteristics from the different approaches, for example as in the case of the exact determination of the baseline of the ECG/1/ for determining the starting point of the P wave, and of the determination, following thereupon, of the duration of the P wave, which return altogether substantially diverging results, depending on the quality of the method used. The patent specifications are, inter alia, DE 43 10 412 (evaluation of the ST segment and/or of the T wave), DE 39 27 709 (evaluation of the ST segment), U.S. Pat. No. 5,159,932 (filtering of the ECG, QRS finding, averaging) or U.S. Pat. No. 5,020,540 (analysis of the frequency structure of the QRST complexes, waveform template). Further relevant patent specifications include the determination of individual characteristics of the ECG and/or serve to detect limited diagnostic statements, for example in U.S. Pat. No. 4,930,075 (evaluation of the ST segment for establishing ischemias), U.S. Pat. No. 5,025,794 (method for bidirectional filtering for the purpose of detecting late potentials), U.S. Pat. No. 5,355,891 (automatic signal averaging by impact triggering for the purpose of detecting late potentials), U.S. Pat. No. 5,341,811 (HP filtering of at least two channels, weighted averaging, use of adaptive filters for common-mode rejection, late potential detection) or DE 43 04 269 (evaluation of the ST segment for assessing acute ischemic damage).

The signal characteristics determined are printed out on the paper strip or displayed directly together with the signal profile of the ECG. For the purpose of outputting diagnostic indications, the individual signal characteristics determined are combined with one another to form sensible diagnostic indications in a more or less complicated and branched decision tree. This is performed, for example, by the programs on which computer ECG units are based. Such decision trees can have the following form, for example: "if parameter 1 occurs in conjunction with parameter 3 and/or parameter 4, and condition 1 is simultaneously active in the medical recording a, it is possible to infer the diagnostic statement xyz therefrom". It is possible in this way to construct a decision tree for each known diagnosis on the basis of individual signal characteristics determined from the ECG in its recordings. Because of the multiplicity of the influencing quantities and parameters, this method is extremely complicated and presupposes extensive cardiological knowledge and/or experience. Changes or improvements to the methods for determining individual parameters, influencing empirically determined threshold values or new medical knowledge require program changes and function tests which are complicated in part, and are therefore associated with high costs and/or require new ECG units with the reworked programs. U.S. Pat. No. 5,355,892 therefore describes an ECG system with portable storage media (floppy disk drive) for storing both ECG and patient information, for example for hospital information systems, and also for reloading or upgrading algorithms for ECG evaluation.

U.S. Pat. No. 5,437,278 describes a medical diagnostic system in which digitized medical data on the state of a patient are compared with likewise digitized medical data which are stored in the memory and determined at an earlier point in time. A diagnosis relating to the patient is derived from the comparison.

The invention is based on the formulated problem of permitting periodic or quasiperiodic signals to be evaluated by means of improved signal comparisons in a way which is independent of medical arguments which are not finally authenticated, and can be done in automated form.

According to the invention, in order to solve this problem the method of the type mentioned at the beginning is characterized in that the periods of the measured signals are normalized to a predetermined period length, and in that the values, digitized with the aid of a specific sampling frequency, of a section of the measured signals, which are normalized to the predetermined period length, are compared with values, formed for the same sampling frequency, of a corresponding section of signals which are stored in a database and normalized to the same predetermined period length.

The evaluation, according to the invention, of measured signals for the purpose of achieving diagnostic information is therefore performed exclusively by a signal comparison with signal patterns stored in the database.

In order to improve the comparability of the measured signals with corresponding signals stored in a database, according to the invention the reference signals of the database are normalized to a predetermined period length and digitized with the aid of a predetermined sampling frequency. In a corresponding way, the measured signals are normalized to the same predetermined period length and digitized with the aid of the same sampling frequency. The comparison of corresponding signals of different patients, in particular, is possible for the first time in this way.

For multichannel measurements such as occur, for example, in the case of the ECG or EEG, it is expedient to undertake the evaluation for individual sensor channels with the aid of stored signal sections of the corresponding or at least comparable sensor channels.

The comparison of the currently measured signal pattern with the signals stored in databases is preferably performed by calculating a correlation coefficient for each section of the measured signals with the aid of the signals of all the signal patterns, or of selected signal patterns stored in the database, and specifically at one point or a plurality of points, the correlation coefficient being used as a measure of the similarity of the compared signals. As a result, only a portion of the diagnostic information contained in the measured signal pattern is used, but, in return, use is made of a simple and quick method which permits the numerous comparisons required to be carried out. If a plurality of correlation coefficients are determined, the maximum of the correlation coefficients is preferably used as a measure of the similarity.

In order to carry out a comparison via a correlation function, the measured data to be compared are displaced toward one another in order thus to form the correlation function in a way known per se.

It is conceivable likewise to convert the signal patterns stored in the database, which have all been digitized with the aid of the same sampling frequency, to a normalized period length for the purpose of the comparison which is respectively to be carried out. However, it is more advantageous for the signal patterns stored in the database to be stored already as data which are normalized to the specific period length and appropriately digitized.

The method according to the invention offers the possibility of using the signal comparison to infer a medical finding by virtue of the fact that the signals stored in the database are assigned medical findings and that after a multiplicity of performed comparisons an accumulation of correspondences between stored signals and a specific medical finding is used to derive a probability for the presence of the specific medical finding with reference to the measured signals.

Figure 2:
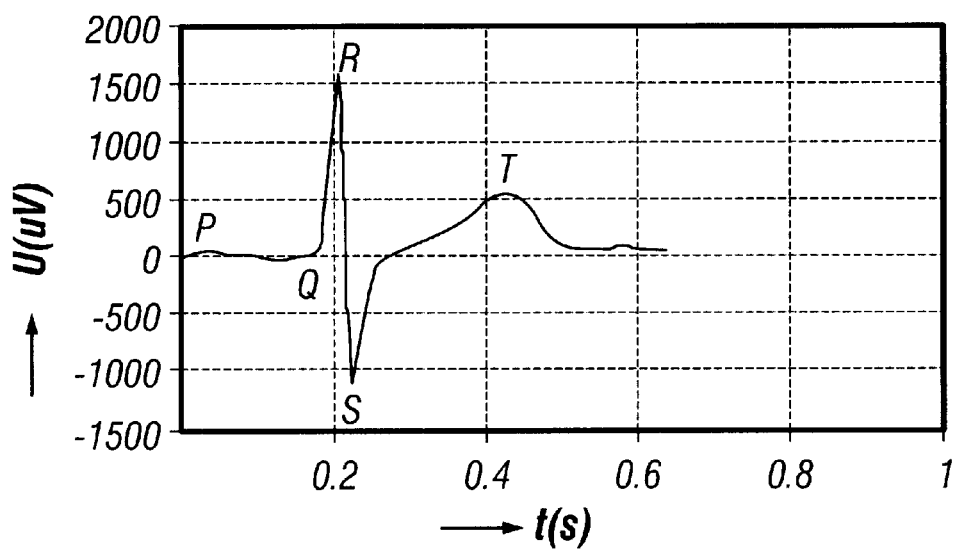
Figure 3:
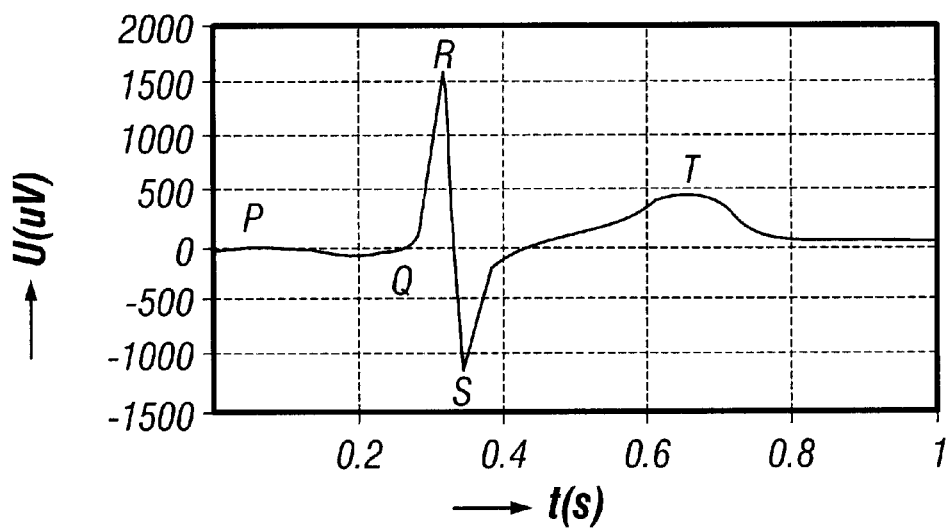
Figure 4:
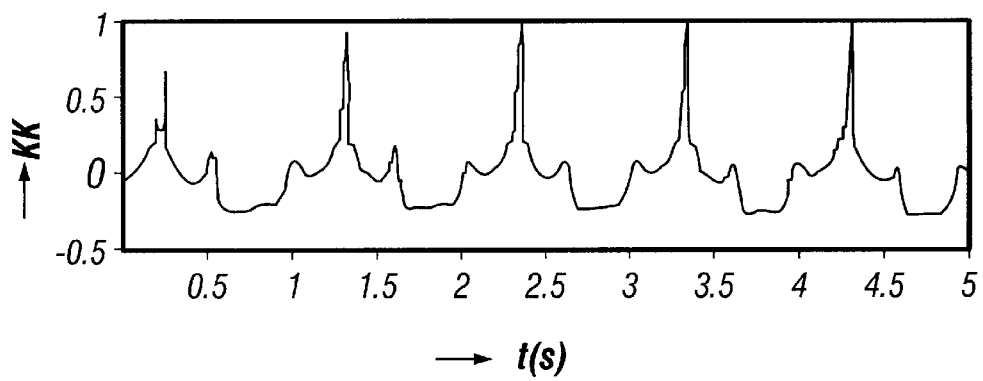
Figure 5:
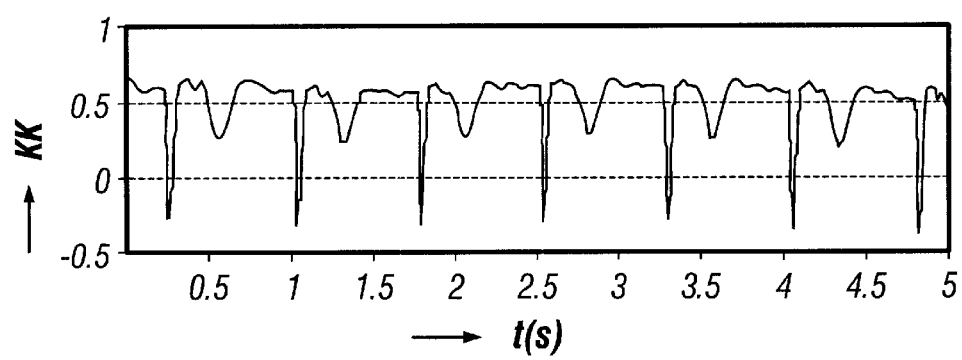

Exemplary embodiment:

The invention is to be explained in more detail below with reference to an exemplary embodiment. In the associated drawings, FIG. 1 shows a diagrammatic illustration of the method steps with reference to the example of the ECG, FIG. 2 shows an illustration of a beat on a recording of an ECG to be compared, before normalization, FIG. 3 shows an illustration of a beat on a recording of an ECG to be compared, after normalization, FIG. 4 shows an illustration of the correlation function of two well-correlated recordings of ECGs of different patients, and FIG. 5 shows an illustration of the correlation function of two poorly-correlated recordings of ECGs of different patients.

In the following exemplary embodiment, the individual method steps are illustrated with reference to the electrocardiogram (FIG. 1). The aim of a comparison for ECG signals is to find for each recording of a measured ECG the or those comparable recordings of ECGs in an ECG database which exhibit the greatest degree of correspondence with reference to their signal patterns. This is performed after a normalization of the ECG signals by calculating the correlation function, which supplies a measure of the correspondence of the signal patterns of two signal sections.

Since each ECG has an individual rhythm independently of the basic signal pattern, and/or strong fluctuations in the cardiac rhythm can occur even within one ECG, it is not possible to compare patterns directly by calculating the correlation function. However, even in the case of identical signal patterns of different heart rates of the recordings to be compared, the direct calculation of the correlation function leads to differing results. In order, nevertheless, to render a comparison possible, the information contained in the signal pattern of the ECG is separated from that contained in the signal rhythm. This renders it possible, by normalizing the signal patterns of the ECG of different patients (with a different heart rate) for example to a uniform, fictitious heart rate, for the ECGs to be compared with one another with regard to their signal pattern by means of correlation.

In practice, this is performed by "compressing" or "stretching" the time axis of comparable signal sections of the recordings of the database ECG, and also of the measured ECG to an identical, fictitious length.

Starting, for example, from one beat as a comparable signal section (FIG. 2 and FIG. 3), the RR intervals of the recordings to be compared are, for example, compressed or stretched to the unit length 1. However, during this adaptation of the time axis the sampling frequency thereof varies owing to the prescribed number of samples of the recording. Since the calculation of the correlation function presupposes identical sampling frequencies of the signal sections to be compared, a recalculation of the samples (resampling) of the compressed or stretched recording of the measured ECG, for example by linear interpolation, is required.

As a result of this mode of procedure, recordings with, for example, an individually distinguishable heart rate (different RR interval) but with the same signal pattern produce the same results in the calculation of the correlation function.

The correlation functions are calculated for each derivative of the reference ECG with the aid of the corresponding recordings of each database ECG, for example by using Equation (1) and (2).

$$K = K(kT_a) 1 \leq k \leq N \tag{1}$$

$$K = \frac{1}{N} \frac{\sum_{n=1}^{N} x_n y_n - \sum_{n=1}^{N} x_n \sum_{n=1}^{N} y_n}{\sqrt{\frac{1}{N} \left[\sum_{n=1}^{N} x_n^2 - \left(\sum_{n=1}^{N} x_n\right)^2\right] \left[\sum_{n=1}^{N} y_n^2 - \left(\sum_{n=1}^{N} y_n\right)^2\right]}} \tag{2}$$

The variables $X_n$ and $Y_n$ characterize the discrete data records which are extracted from the reference ECG X to be evaluated, and the database ECG Y. The number of points N at which the function can be formed follows from the length of the signal sections to be compared. One period of the ECG signal is used, for example, for the signal pattern section of each recording of the ECG to be compared. The comparability of ECGs which include a plurality of recordings, requires that the time intervals of each recording which are used are extracted at the same instant within the ECG. The extracted period contains, for example, the signal sections P wave, QRS complex and T wave. After normalization of the timescale, this signal pattern is compared with at least one beat period of the database ECG. The correlation function is, once again, a periodic function in accordance with periodic behavior of the database ECG. FIG. 4 shows the profile of the correlation function in the case when signal patterns of the correlated ECG derivatives exhibit good correspondence. The periodically recurring maxima at the points of the greatest correspondence of the signal patterns with an amplitude value close to the value 1 are clearly expressed. FIG. 5 shows, by contrast, the correlation function for the case of signal patterns which correspond less well. The amplitudes of the positive maxima of the correlation function are here below the value 0.5.

In accordance with the set objects formulated at the beginning, the signal patterns exhibiting good correspondence are sought. For this reason, only the positive maximum values $M_i$ of the correlation function is determined. These maxima are sought by evaluating the amplitudes whilst simultaneously observing the periodicity of the signal. The amplitudes of the periodic maxima $M_i$ deviate from one another as a function of the differences of the individual ECG beats of a recording from one another (beat variation).

Consequently, in a further step the absolute maximum M of the periodic maxima $M_i$ is sought in accordance with equation (3):

$$M = \max_{i=1}^{k} (M_i) \qquad (3)$$

The quantity M thus obtained is a measure of the correspondence of the derivatives which are to be compared with one another.

The greater the degree of similarity of the signal patterns, the greater is the value of M. M=1 in the case of complete correspondence between the patterns. The results of these calculations lead to a table (Table 1) whose column elements maintain for each derivative the absolute maximum value M of the respective correlation function according to Equation (1). The rows of this table are formed by the database ECG used for the comparison. An EGC number serves to identify the database ECG.

corresponds to the recording V1 lead of the reference ECG with the maximum correlation $M_{v1}$=0.93444, whereas the recording V4 lead corresponds only with $M_{v4}$=0.21569.

It is clear to the person skilled in the art of medicine that ECG signals measured regularly at rest can be compared. ECG signals recorded when a patient is exercising undergo a variation in the signal shape which remains largely without variation as regards the systole but, because of the higher heart rate, is greatly shortened with regard to the diastole. If exercise ECGs are to be included in the comparison, the corresponding signal variation for these patients must be taken into account in the evaluation by the exercise by comparison with the resting ECG.

What is claimed is:

1. Method for evaluating measured periodic or quasiperiodic signals of medical sensor systems, comprising the steps of:
    digitizing the measured signals with a specific first sampling frequency;
    normalizing the periods of the measured signals to a predetermined period length;
    using a database in which previously measured signals are stored after digitization with specific second sampling frequencies and in which medical findings are assigned to the stored signals;
    if the first and second sampling frequencies are not identical, converting the measured signal of the signals stored in the database so as to have the same sampling frequencies;
    comparing at least a section of the digitized measured signal with a corresponding section of the signals stored in the database;
    determining an accumulation of correspondences between stored signals and the measured signals and determining a correspondence accumulation of medical findings assigned to said stored signals; and
    deriving a probability for the presence of a specific medical finding with reference to the measured signal from the degree of accumulation.

2. Method according to claim 1, characterized in that signal sections of different patients are compared with one another.

3. Method according to claim 1, characterized in that multichannel measurements signals of individual sensor channels are compared with stored signals of comparable sensor channels.

TABLE 1

Example for the representation of the correlation results (reference ECG No. 281)

| ECG No. | V1 | V2 | V3 | V4 | V5 | V6 | VX | VY | VZ |
| --- | --- | --- | --- | --- | --- | --- | --- | --- | --- |
| 1 | 0.9344 | 9.7158 | 0.4716 | 0.2156 | 0.6730 | 0.8551 | 0.8770 | 0.6391 | 0.8739 |
| 2 | 0.9353 | 0.9137 | 0.8456 | 0.4659 | 0.3440 | 0.6359 | 0.6288 | 0.4124 | 0.9115 |
| 3 | 0.9296 | 0.9026 | 0.5757 | 0.2566 | 0.7614 | 0.8955 | 0.8869 | 0.5512 | 0.8500 |
| 4 | 0.5581 | 0.3083 | 0.1820 | 0.2385 | 0.8575 | 0.9194 | 0.9036 | 0.4272 | 0.3108 |
| 5 | 0.8924 | 0.6752 | 0.4599 | 0.3656 | 0.5817 | 0.8003 | 0.8309 | 0.4432 | 0.7508 |
| 6 | 0.9248 | 0.8974 | 0.5654 | 0.2641 | 0.7069 | 0.8335 | 0.9018 | 0.5178 | 0.8711 |
| 7 | 0.8833 | 0.8781 | 0.7909 | 0.5580 | 0.5524 | 0.8212 | 0.8196 | 0.5462 | 0.7597 |
| 8 | 0.4268 | 0.4237 | 0.4057 | 0.4549 | 0.5289 | 0.8297 | 0.7654 | 0.7184 | 0.3415 |
| 9 | 0.8841 | 0.9335 | 0.6990 | 0.4231 | 0.4224 | 0.6012 | 0.5294 | 0.8438 | 0.9500 |
| 10 | 0.3402 | 0.3667 | 0.2604 | 0.4037 | 0.6145 | 0.3932 | 0.4683 | 0.4891 | 0.7384 |

Table 1 shows the results of the pattern comparison for the first 10 database ECGs and for the recordings V1–V6 leads and the Frank recordings Vx, Vy, leads. It may be read off therefrom for the database ECG 1 that the recording V1 lead 4. Method according to claim 1, characterized in that for each section of the measured signals, at one point or a plurality of points a correlation coefficient is calculated with the aid of the signals of all signal patterns or of selected signal patterns stored in the database, and used as a measure of the similarity of the compared signals.

5. Method according to claim 4, characterized in that a correlation function is formed from correlation coefficients which have been determined.

6. Method according to claim 4, characterized in that during calculation of a plurality of correlation coefficients their maximum is used as a measure of the similarity of the compared signals.

7. Method according to claim 1, characterized in that the signal patterns stored as data, in the database, are normalized to the specific period length and appropriately digitized.

8. Method according to claim 1, characterized in that in a case of ECG signals, the period length in the signal pattern is selected in accordance with a RR interval and/or the mean value of a plurality of RR intervals.

9. Method according to claim 1, characterized in that in a case of ECG signals with an R peak position which can be established, a correlation coefficient is determined only at the point at which the R peaks of the regions to be compared are superimposed on one another.

10. Method according to claim 1, characterized in that in a case of ECG signals without an R peak position which can be established, a correlation function is calculated over at least one period of the ECG signal.

11. Method according to one of claim 1, characterized in that the signals stored in the database are assigned medical findings, and in that after a multiplicity of performed comparisons an accumulation of correspondences between stored signals and a specific medical finding is used to derive a probability for the presence of the specific medical finding with reference to the measured signals.

12. Method according to claim 11, characterized in that the length of the sections is selected such that they include only a portion of a diagnostic piece of information.

* * * * *